US006531304B1

(12) United States Patent
Bönnemann et al.

(10) Patent No.: US 6,531,304 B1
(45) Date of Patent: Mar. 11, 2003

(54) METHOD FOR MODIFYING THE DISPERSION CHARACTERISTICS OF METAL ORGANIC-PRESTABILIZED OR PRE-TREATED NANOMETAL COLLOIDS

(75) Inventors: Helmut Bönnemann, Essen (DE); Werner Brijoux, Oberhausen (DE); Rainer Brinkmann, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/700,525

(22) PCT Filed: May 14, 1999

(86) PCT No.: PCT/EP99/03319

§ 371 (c)(1),
(2), (4) Date: Nov. 15, 2000

(87) PCT Pub. No.: WO99/59713

PCT Pub. Date: Nov. 25, 1999

(30) Foreign Application Priority Data

May 18, 1998 (DE) ........................................ 198 21 968

(51) Int. Cl.[7] .......................... B01F 17/00; B01J 13/00; C12N 13/00; H01F 1/44; H01M 4/92

(52) U.S. Cl. ............................... 435/173.9; 106/31.92; 252/62.55; 427/216; 423/219; 428/570; 429/43; 502/173; 516/33; 516/78; 516/97; 604/113

(58) Field of Search ............................. 516/33, 78, 97; 252/62.55; 502/173; 427/216; 428/570; 128/204.19; 106/31.92; 429/43; 607/103; 96/1; 423/219; 604/113; 435/173.9

(56) References Cited

U.S. PATENT DOCUMENTS

| | | | | | |
|---|---|---|---|---|---|
| 3,682,585 | A | * | 8/1972 | Frevel et al. | 423/219 |
| 4,812,767 | A | * | 3/1989 | Taketomi | 324/244 |
| 5,580,492 | A | * | 12/1996 | Bönnemann et al. | 516/33 |
| 5,702,630 | A | * | 12/1997 | Sasaki et al. | 252/62.55 X |
| 5,814,370 | A | * | 9/1998 | Martino et al. | 427/216 X |
| 5,858,595 | A | * | 1/1999 | Ziolo | 106/31.92 X |
| 6,045,925 | A | * | 4/2000 | Klabunde et al. | 427/216 |

FOREIGN PATENT DOCUMENTS

WO WO91/09678 * 7/1991

OTHER PUBLICATIONS

Bönnemann Et Al.: "Preparation and Catalytic Properties of $NR_{4^+}$—Stabilized Palladium Colloids", Applied Organometallic Chemistry, vol. 8, 361–378, 1994.*

Schmidt Et Al.: "PtRu Alloy Colloids as Precursors for Fuel Cell Catalysts", J. Electrochem. Soc., vol. 145, No. 3, Mar. 1998.*

* cited by examiner

*Primary Examiner*—Richard D. Lovering
(74) *Attorney, Agent, or Firm*—Norris McLaughlin & Marcus

(57) ABSTRACT

The present invention relates to a process for modifying the dispersing properties of organometallic-prestabilized or organometallic-pretreated nanometal colloids by reacting reactive metal-carbon bonds in the protective shell to prepare nanometal colloids having a wide range of solubilities in hydrophilic and hydrophobic media including water, to the colloids thus prepared and their use.

25 Claims, No Drawings

METHOD FOR MODIFYING THE DISPERSION CHARACTERISTICS OF METAL ORGANIC-PRESTABILIZED OR PRE-TREATED NANOMETAL COLLOIDS

This application is a 371 of PCT/EP99/03319, which was filed on May 14, 1999.

The present invention relates to the preparation of nanoscale transition metal or alloy colloids having a high dispersibility in different solvents, to the colloids thus obtained and their use.

Nanoscale transition metal or alloy colloids are of technical importance as precursors of homogeneous and heterogeneous chemical catalysts, as catalysts in fuel cell technology, further as materials for coating surfaces (especially in lithography and in touch-sensing technology), as ferrofluids, e.g., in vacuum-tight rotational bushings, in active vibration dampers (automobile construction), and in tumor control using magnetically induced hyperthermia. They further serve as starting materials in sol/gel technology.

The technically advantageous universal use of nanostructured monometal and multimetal particles requires the decomposition-free redispersibility of the metal particles in a high metal concentration in a wide range of hydrophobic and hydrophilic solvents including water.

There have been many attempts to selectively change the dispersing properties of nanoscale transition metal or alloy colloids. Thus, G. Schmid et al. and C. Larpent et al. as well as N. Toshima et al. describe the conversion of hydrophobic metal colloids to water-soluble colloid systems by exchanging hydrophobic with hydrophilic protective shells through extractive ligand exchange at the interface between the organic and aqueous phases [e.g., G. Schmid et al., Polyhedron Vol. 7 (1988) p. 605–608; G. Schmid, Polyhedron Vol. 7 (1988) p. 2321; C. Larpent et al., J. Mol. Catal., 65 (1991) L 35; N. Toshima et al., J. Chem. Soc., Chem. Commun. (1992), p. 1095]. However, this kind of protective shell exchange allows only for the replacement of hydrophobic by hydrophilic ligands and vice versa, but does not enable the decomposition-free redispersibility of the metal particles in a high metal concentration in a wide range of hydrophobic and hydrophilic solvents including water. Thus, the problem of repeptization of nanoscale transition metal or alloy colloids in any solvents cannot be solved by ligand exchange. For the stabilization of metal, metal oxide and metal sulfide colloids, Antonietti et al. (PCT/EP 96/00721, WO 96/26004) use block copolymers as micelle builders in organic (e.g., toluene, cyclohexane, THF) or inorganic solvents (e.g., water, liquid ammonia). The nature of the respective side chains of the micelles restricts the solubility of the colloids to either organic or inorganic media. Thus, this way does not enable a broad solubility range either.

Chagnon (U.S. Pat. No. 5,147,573) describes the preparation of electrically conducting superparamagnetic colloidal dispersions from solid magnetic particles by adsorptive coating with (water-stable) organometallics, e.g., $Sn(C_2H_5)_4$, in water, followed by reaction with dispersing aids (e.g., surfactants) and addition of an organic carrier liquid, such as toluene. This method does not result in isolatable metal colloids and is not applicable to precious metals (see Comparative Example 4).

It has been the object of the present invention to provide a process which overcomes the above mentioned difficulties and enables the selective modification of the dispersing properties of nanoscale transition metal or alloy colloids for a decomposition-free repeptization of the colloids, modified and isolated with retention of the size distribution, in any desired hydrophobic or hydrophilic solvents including water for further technical processing in as high as possible a concentration.

It has now been found that colloids which are dispersible in a wide range of hydrophobic and hydrophilic solvents including water are formed by reading reactive metal-carbon bonds in the protective shell of organometallic-prestabilized transition metal or alloy colloids, prepared by known synthetic methods, of metals of Periodic Table groups 6 to 11 [e.g., K. Ziegler, Brennstoffchemie 35 (1954) p. 322, cf. K. Ziegler, W. R. Kroll, W. Larbig, O. W. Steudel, Liebigs Annalen der Chemie, 629 (1960) p. 74, and Houben-Weyl, Methoden der organischen Chemie, E. Müller (ed.), Volume 13/4, Thieme Verlag Stuttgart (1970) p. 41; J. S. Bradley, E. Hill, M. E. Leonowic, H. Witzke, J. Mol. Catal. 41 (1987) p. 59–74; J. Barrault, M. Blanchart, A. Derouault, M. Kisbi, M. I. Zaki, J. Mol. Catal. 93 (1994) p. 289–304] or of organometallic-prestabilized and organometallic-pretreated transition metal or alloy colloids (Periodic Table groups 6 to 11) presynthesized by known synthetic methods [e.g., J. S. Bradley, Clusters and Coloids, Ed.: G. Schmid, VCH Weinheim (1994) p. 459–536], hereinafter referred to as starting materials, with a chemical modifier. Suitable chemical modifiers include materials capable of protolysis of metal-carbon bonds [cf. F. A. Cotton, G. Wilkinson; Advanced Inorganic Chemistry, John Wiley & Sons, New York, 4th ed. (1980) p. 344; Ch. Eischenbroich, A. Salzer; Organometallchemie, B. G. Teubner, Stuttgart (1986) p. 93] or of insertion of C/C, C/N or C/O multiple bonds in metal-carbon bonds [G. Wilkinson, F. G. A. Stone; Comprehensive Organometallic Chemistry, Vol. 1, Pergamon Press, Oxford (1982) p. 637, p. 645, p. 651] or of Lewis acid-base interactions with metal carbon bonds [Ch. Elschenbroich, A. Salzer; B. G. Teubner, Stuttgart (1986) p. 95; G. Wilkinson, F. G. A. Stone; Comprehensive Organometallic Chemistry, Vol. 1, Pergamon Press, Oxford (1982) p. 595].

The starting materials can be prepared by reacting metal salts, halides, pseudohalides, alcoholates, carboxylates or acetylacetonates of metals of Periodic Table groups 6 to 11 with protolyzable organometallic compounds. Alternatively, for preparing the starting materials, colloids of transition metals of Periodic Table groups 6 to 11 synthesized by other methods, e.g., precious-metal anticorrosion-protected colloids of Fe, Co, Ni or their alloys, may be reacted with organometallic compounds. The protective shell of the thus prepared colloidal starting materials contains reactive metal-carbon bonds which can react with the modifiers (see Example 1, protolysis experiment). Non-colloidal solid metal particles or powders (cf. Chagnon, U.S. Pat. No. 5,147,573) cannot be reacted by the process according to the invention (Comparative Examples 1, 2 and 3). Suitable organometallic compounds include protolyzable organoelement compounds of metals of Periodic Table groups 1 or 2 and 12 and 13.

Suitable chemical modifiers with which these organometallic-prestabilized starting materials are reacted to achieve a high dispersibility (at least 20 mmol of metal per liter, preferably >100 mmol of metal per liter) include, for example, alcohols, carboxylic acids, polymers, polyethers, polyalcohols, polysaccharides, sugars, surfactants, silanols, active charcoals, inorganic oxides or hydroxides. A particular characteristic of the modification process according to the invention is the retention of particle size.

According to the invention, the reaction of the organometallic-prestabilized starting materials with such modifiers may also be effected in situ, i.e., without intermediate isolation of the starting materials.

As determined by elemental analysis (cf., e.g., Example 9), the protective shells of the transition metal or alloy particles modified according to the invention consist of metal compounds of the modifier with the elements of the organometallic compounds employed for prestabilization (Periodic Table groups 1 or 2 and 12 and 13, for example, Al or Mg; cf. Table 3, Nos. 18, 19, 24, 26, 29 and 30).

The modification process performed according to the invention permits the preparation of novel nanostructured transition metal or alloy colloids the dispersing properties of which are tailored to match the respective intended technical use. For example, the modification according to the invention of the organoaluminum-prestabilized Pt colloid used as the starting material (Table 1, No. 22) with polyoxyethylene sorbitan monopalmitate (Tween 40, Table 2, No. 15) yields a novel Pt colloid with a very wide dispersing range which can be redispersed both in lipophilic solvents, such as aromatics, ethers and ketones, and in hydrophilic media, such as alcohols or pure water, in concentrations of >100 mmol of Pt per liter without precipitation of metal (Table 3, No. 20).

In contrast, the modification according to the invention of the same organoaluminum-prestabilized Pt colloid used as the starting material with decanol or oleic acid (Table 2, Nos. 1 and 3) yields a Pt colloid with excellent redispersibility especially in engineering pump oils (Table 3, Nos. 7 and 9). The modification according to the invention of the same starting material with polyethylene glycol PEG 200, polyvinyl pyrrolidone, surfactants of the cationic, anionic or non-ionic-types or with polyalcohols, e.g., glucose (Table 2, Nos. 5–7, 9–11, 13 and 14), yields Pt colloids with excellent dispersing properties predominantly in aqueous media (Table 3, Nos. 10–12, 14–16, 18–20).

The dispersing properties of organoaluminum-prestabilized Fe bimetallic colloids can also be selectively adapted to their intended technical use by means of the modification according to the invention: Thus, the reaction of the $Fe_2Co$ organosol used as the starting material (Table 1, No. 34) with decanol (Table 2, No. 1) results in colloidal $Fe_2Co$ with advantageous dispersibility in special pump oils (Shell Vitrea Oil 100, Shell) as employed in-technical magnetic fluid seals (Table 3, No. 27). According to the invention, the organoaluminum-treated presynthesized Fe/Au organosol (Example 13, MK 41) as a starting material can be converted by modification with polyethylene glycol dodecyl ether to a hydrosol which can be redispersed without decomposition in physiologically relevant media, such as ethanol/water mixtures (25/75 v/v), in a high concentration (>100 mmol of metal per liter) (Table 3, No. 28).

The modification according to the invention of the organoaluminum-prestabilized Pt/Ru colloid used as the starting material (Table 1, No. 36) and having an average particle size of 1.3 nm as determined by TEM (transmission electron microscopy) with polyethylene glycol dodecyl ether yields a novel Pt/Ru colloid having the same average particle size of 1.3 nm as determined by TEM and being equally well dispersible in aromatics, ethers, acetone, alcohols and water (Example 11, Table 3, No. 29). As determined by TEM, the modification process according to the invention of the protective shell is effected with full retention of particle size even for very small particles.

Nanoscale transition metal or alloy colloids having protective shells modified according to the invention can be employed to technical advantage as precursors for the preparation of homogeneous and heterogeneous chemical catalysts. Nanoscale Pt or Pt alloy colloids having an average particle diameter of <2 nm as determined by TEM (Examples 11 and 12, Table 3, Nos. 29 and 30) are suitable precursors for fuel cell catalysts. Nanoscale Fe, Co, Ni or alloy colloids (Examples 3 and 10, Table 3, Nos. 2 to 4 and 27) and gold-protected Fe (Example 13, Table 3, No. 28), Co, Ni or alloy colloids are employed in the magneto-optical storage of information and as magnetic fluids in magnetic fluid seals. Fe colloids (Example 13, Table 3, No. 2) and gold-protected Fe colloids (Example 13, Table 3, No. 28) serve as magnetic cell markers and for magnetic cell separation. Fe colloids (after treatment with oxygen, if necessary) and gold-protected Fe colloids with modified protective shells have fields of application in medical tumor therapy (magnetic fluid hyperthermia). Nanoscale transition metal or alloy colloids, especially of platinum, are employed as metallic inks in ink-jet printers and for laser sintering, for example, by coating quartz plates with the sol and sintering the dried layers with a $CO_2$ laser to give a conductive metallic layer. Further, nanoscale transition metal or alloy colloids modified according to the invention are suitable for the coating of surfaces and for use in sol-gel processes.

The following non-limiting Examples illustrate the invention:

COMPARATIVE EXAMPLE 1

1.65 g (23 mmol) of magnetic Co nanopowder is suspended in 300 ml of toluene under argon as a protective gas, and 0.4 g (5.5 mmol) of $AlMe_3$ is added. With stirring, 0.4 g (1.4 mmol) of oleic acid is pipetted thereto at 20° C., and the mixture is heated to 70° C. for 30 minutes. A colorless reaction solution with undissolved Co powder is obtained (no colloid formation).

COMPARATIVE EXAMPLE 2

The same procedure is used as in Comparative Example 1, except that 1.63 g (23 mmol) of magnetic Ni nanopowder is used to obtain a slightly turbid colorless solution with undissolved Ni powder (no colloid formation).

COMPARATIVE EXAMPLE 3

The same procedure is used as in Comparative Example 1, except that 5.46 g (23 mmol) of Pt nanopowder is used to obtain a slightly turbid colorless solution with undissolved Pt powder (no colloid formation).

Comparative Example 4

(Corresponding to U.S. Pat. No. 5,147,573, Example 2)

5.46 g of Pt nanopowder is suspended in 30 ml of water, and 0.4 g (1.7 mmol) of $SnEt_4$ is added at 20° C. After 5 minutes of stirring, 0.4 g (1.4 mmol) of oleic acid is added, and the mixture is heated to 70° C. for 30 minutes to form a white milky reaction mixture with undissolved Pt nanopowder. The addition of toluene does not result in colloidal Pt metal being extracted therefrom. A colorless toluene phase is obtained.

EXAMPLE 1

Preparation of Pt Colloid from $Pt(acac)_2$ and $AlMe_3$ (Protolysis Experiment)

Under argon as a protective gas, 3.83 g (10 mmol) of $Pt(acac)_2$ is dissolved in 100 ml of toluene in a 250 ml flask, and 2.2 g (30 mmol) of $AlMe_3$ in 50 ml of toluene is added dropwise at 40° C. within 24 h. The mass-spectroscopical analysis of the 438 standard ml of reaction gas yields a composition of 84% by volume of methane, 7.4% by volume of ethene, 4.0% by volume of ethane, 2.3% by volume of propene and 2.2% by volume of hydrogen. Then, any volatile matter is distilled off in vacuo (0.1 Pa) to obtain 6.1 g of Pt colloid in the form of a black powder. Metal content: Pt: 30.9% by weight, Al: 13.4% by weight (Table 1, No. 40).

The Pt colloid thus obtained was protolyzed with 200 ml of 1 N hydrochloric acid to obtain 1342 standard ml of gas having a composition of 95.9% by volume of methane and 4.1% by volume of $C_2$–$C_3$ gases.

Balance: employed: 90 mmol of methyl groups found: 22.3 mmol of reaction gas, calculated as $C_1$
62.9 mmol of protolysis gas, calculated as $C_1$
85.2 mmol of total gas corresponds to 94.7% of theory, based on $CH_3$ groups employed.

EXAMPLE 2

Preparation of Cr Colloid from $Cr(acac)_3$, $AlMe_3$ and Modifier No. 13

Under argon as a protective gas, 2.5 g (7.2 mmol) of $Cr(acac)_3$ is dissolved in 100 ml of toluene in a 250 ml flask, and 3.5 g (50 mmol) of $AlMe_3$ in 50 ml of toluene is added dropwise at 20° C. within 1 h. After 2 h of allowing the reaction to complete, any volatile matter is distilled off in vacuo (0.1 Pa) to obtain 2.9 g of Cr colloid in the form of a black powder. It is soluble in acetone, THF and toluene (Table 1, No. 1). 0.52 g (1 mmol) of this Cr colloid MK 1 is dissolved in 200 ml of THF, 2.0 g of modifier No. 13 (Table 2) is added, and the mixture is stirred at 60° C. for 16 h. Any volatile matter is separated off in vacuo (0.1 Pa) to obtain 3.2 g of modified Cr colloid in the form of a black-brown viscous substance. It is soluble in toluene, THF, methanol and ethanol (Table 3, No. 1).

EXAMPLE 3

Preparation of Ni Colloid from $Ni(acac)_2$, $AlMe_3$ and Modifier No. 13

Under argon as a protective gas, 2.57 g (10 mmol) of $Ni(acac)_2$ is dissolved in 100 ml of toluene in a 250 ml flask, and 2.1 g (30 mmol) of $AlMe_3$ in 50 ml of toluene is added dropwise at 20° C. within 3 h. After 2 h of allowing the reaction to complete, any volatile matter is distilled off in vacuo (0.1 Pa) to obtain 2.6 g of Ni colloid in the form of a black powder. It is soluble in acetone, THF and toluene (Table 1, No. 4). Under argon as a protective gas, 0.39 g (1 mmol) of this Ni colloid MK 4 is dissolved in 100 ml of THF in a 250 ml flask, 2.0 g of modifier No. 13 (Table 2) is added, and the mixture is stirred at 60° C. for 16 h. Any volatile matter is separated off in vacuo (0.1 Pa) to obtain 1.1 g of modified Ni colloid in the form of a black-brown viscous substance. It is soluble in toluene, THF, methanol, ethanol and acetone (Table 3, No. 4).

EXAMPLE 4

Preparation of Pd Colloid from $Pd(acac)_2$, $AlMe_3$ and Modifier No. 13

The same procedure is used as in Example 2, except that 0.3 g (1 mmol) of $Pd(acac)_2$ in 300 ml of THF is used, 0.14 g (2 mmol) of $AlMe_3$ in 50 ml of THF as a reductant is added dropwise at 20° C. within 5 h to obtain 0.39 g of Pd colloid in the form of a black solid powder. Metal content: Pd: 27% by weight, Al: 14% by weight (Table 1, No. 13). 0.39 g (1 mmol) of this Pd colloid MK 13 is dissolved in 300 ml of THF, and 1 g of modifier No. 13 (Table 2) is added at 20° C., and the mixture is stirred for 16 h to obtain 1.4 g of modified Pd colloid in the form of a brown solid. It is soluble in toluene, ether, THF and acetone (Table 3, No. 6).

EXAMPLE 5

Preparation of Pt Colloid from $Pt(acac)_2$, $AlMe_3$ and Modifier No. 3

The same procedure is used as in Example 1, except that 7.88 g (20 mmol) of $Pt(acac)_2$ in 200 ml of toluene is used, 4.32 g (60 mmol) of $AlMe_3$ in 50 ml of toluene as a reductant is added dropwise at 40° C. within 24 h to obtain 8.3 g of Pt colloid in the form of a black powder. Metal content: Pt: 42.3% by weight, Al: 17.5% by weight (Table 1, No. 22). 0.21 g (0.5 mmol) of this Pt colloid MK 22 is dissolved in 100 ml of THF, and 1.5 g of modifier No. 3 (Table 2) is added at 60° C. within 16 h to obtain 1.4 g of modified Pt colloid in the form of a brown-black viscous substance. It is soluble in pentane, hexane, toluene, ether, THF and pump oil (Table 3, No. 9).

EXAMPLE 6

Preparation of Pt Colloid from $Pt(acac)_2$, $AlMe_3$ and Modifier No. 5

The same procedure is used as in Example 5, except that 0.21 g (0.5 mmol) of Pt colloid MK 22 (Table 1, , No. 22) in 100 ml of THF is used, and 1.5 g of modifier No. 5 (Table 2) is added to obtain 1.0 g of modified Pt colloid in the form of a brown solid (Table 3, No. 10).

EXAMPLE 7

Preparation of Pt Colloid from $Pt(acac)_2$, $Et_2AlH$ and Modifier No. 13

The same procedure is used as in Example 2, except that 0.38 g (1 mmol) of $Pt(acac)_2$ in 100 ml of toluene is used, 0.26 g (3 mmol) of $Et_2AlH$ as a reductant is added dropwise at 20° C. within 23 h to obtain 0.3 g of Pt colloid in the form of a black powder. It is soluble in acetone, THF and toluene (Table 1, No. 25). 0.1 g (0.33 mmol) of this Pt colloid MK 25 is dissolved in 100 ml of THF, and 1 g of modifier No. 13 (Table 2) is added at 20° C., and the mixture is stirred for 16 h to obtain 1.7 g of modified Pt colloid in the form of a brown solid. It is soluble in toluene, ether, THF, ethanol, acetone and water (Table 3, No. 22).

EXAMPLE 8

Preparation of Pt Colloid from $Pt(acac)_2$, $MgEt_2$ and Modifier No. 13

0.38 g (1 mmol) of $Pt(acaC)_2$ is dissolved in 100 ml of toluene, 1.2 g (14.6 mmol) of $MgEt_2$ as a reductant is added at 20° C., and the reaction is allowed to complete for 21 h. Any volatile matter is distilled off in vacuo (0.1 Pa) to obtain 1.2 g of Pt colloid in the form of a black powder. It is soluble in acetone., THF and toluene. Elemental analysis: Pt: 14.9% by weight, Mg: 20.8% by weight, C: 49.2% by weight, H: 7.9% by weight (Table 1, No. 27). 0.56 g (0.5 mmol) of this Pt colloid MK 27 is dissolved in 100 ml of THF, and 2.0 g of modifier No. 13 (Table 2) is added to obtain 2.6 g of modified Pt colloid in the form of a brown-black substance. Elemental analysis: Pt: 4.6% by weight, Mg: 5.6% by weight, C: 74.1% by weight, H: 11.1% by weight. It is soluble in toluene, ether, THF, ethanol, acetone and water (Table 3, No. 24).

EXAMPLE 9

Preparation of Pt Colloid from $PtCl_2$, $AlMe_3$ and Modifier No. 4

The same procedure is used as in Example 2, except that 0.27 g (1 mmol) of $PtCl_2$ in 125 ml of toluene is used, 0.34 g (3 mmol) of $AlMe_3$ as a reductant in 25 ml of toluene is added dropwise at 40° C. within 16 h to obtain 0.47 g of Pt colloid in the form of a black powder. Elemental analysis: Pt: 41.1% by weight, Al: 15.2% by weight, C: 23.4% by weight, H: 4.9% by weight, Cl: 13.6% by weight. Average particle size as determined by TEM: 2 nm (Table 1, No. 30). 0.47 g (1 mmol) of this Pt colloid MK 30 is dissolved in 100 ml of toluene, 1.0 g of modifier No. 4 (Table 2) is added at 60° C., and the mixture is stirred for 3 h to obtain 1.3 g of modified Pt colloid in the form of a brown-black viscous substance. Elemental analysis: Pt: 11.00 by weight, Al: 3.9% by weight, Si: 7.4% by weight, C: 63.1% by weight, H: 4.9% by weight, Cl: 3.4% by weight. It is soluble in toluene, ether and acetone (Table 3, No. 26).

EXAMPLE 10

Preparation of Fe/Co Colloid from $Fe(acac)_2$, $Co(acac)_2$, $AlMe_3$ and Modifier No. 1

Under argon as a protective gas, 2.54 g (10 mmol) of $Fe(acac)_2$ and 1.29 g (5 mmol) of $Co(acac)_2$ are dissolved in 200 ml of toluene in a 500 ml flask, and 5.4 g (75 mmol) of $AlMe_3$ in 50 ml of toluene is added dropwise at 20° C. within 1 h. After 2 h of allowing the reaction to complete, any volatile matter is distilled off in vacuo (0.1 Pa) to obtain 4.9 g of Fe/Co colloid in the form of a black powder. It is soluble in acetone, THF and toluene (Table 1, No. 34). 0.136 g (0.5 mmol) of this $Fe_2Co$ colloid MK 34 is dissolved in 100 ml of THF, 1.5 g of modifier No. 1 (Table 2) is added at 60° C., and the mixture is stirred for 16 h. Any volatile matter is separated off in vacuo (0.1 Pa) to obtain 1.6 g of modified $Fe_2Co$ colloid in the form of an oily brown-black substance. It is soluble in hexane, toluene and pump oil (Table 3, No. 27).

EXAMPLE 11

Preparation of Pt/Ru Colloid from $Pt(acac)_2$, $Ru(acac)_3$, $AlMe_3$ and Modifier No. 13

The same procedure is used as in Example 10, except that 7.86 g (20 mmol) of $Pt(acac)_2$ and 7.96 g (20 mmol) of $Ru(acac)_3$ in 400 ml of toluene is used, 8.64 g (120 mmol) of $AlMe_3$ as a reductant is added dropwise at 60° C. within 21 h to obtain 17.1 g of Pt/Ru colloid in the form of a black powder. Elemental analysis: Pt: 20.6% by weight, Ru: 10.5% by weight, Al: 19.6% by weight, C: 39.1% by weight, H: 5.1% by weight. Average particle size as determined by TEM: 1.3 nm. It is soluble in acetone, THF and toluene (Table 1, No. 36). 0.94 g (1 mmol of Pt, 1 mmol of Ru) of this PtRu colloid MK 36 is dissolved in 100 ml of THF, and 2.0 g of modifier No. 13 (Table 2) is added to obtain 3.2 g of modified PtRu colloid in the form of a black-brown substance. Elemental analysis: Pt: 6.3% by weight, Ru: 3.0% by weight, Al: 5.1% by weight, C: 56.6% by weight, H: 8.3% by weight. Average particle size as determined by TEM: 1.3 nm. It is soluble in toluene (160 mmol/l), ether, THF (110 mmol/l), methanol, ethanol, acetone and water (130 mmol/l) (Table 3, No. 29).

EXAMPLE 12

Preparation of Pt/Sn Colloid from $Pt(acac)_2$, $SnCl_2$, $AlMe_3$ and Modifier No. 13

The same procedure is used as in Example 10, except that 1.15 g (2.9 mmol) of $Pt(acac)_2$ and 0.19 g (1 mmol) of $SnCl_2$ in 100 ml of toluene is used, 0.86 g (12 mmol) of $AlMe_3$ as a reductant is added dropwise at 60° C. within 2 h to obtain 1.1 g of $Pt_3Sn$ colloid in the form of a black powder. Metal content: Pt: 27.1% by weight, Sn: 5.2% by weight, Al: 14.4% by weight (Table 1, No. 39). 0.36 g (0.5 mmol of Pt, 0.17 mmol of Sn) of this $Pt_3Sn$ colloid MK 39 was dissolved in 200 ml of THF, and 1 g of modifier No. 13 (Table 2) is added to obtain 1.4 g of modified $Pt_3Sn$ colloid in the form of a black-brown substance. Metal content: Pt: 6.8% by weight, Sn: 1.2% by weight, Al: 3.3% by weight. It is soluble in toluene, THF, ethanol, acetone and water (Table 3, No. 30).

EXAMPLE 13

Preparation of Fe/Au Colloid from Fe-sarcosine Colloid, $AuCl_3$, $AlEt_3$ and Modifier No. 13

Under argon as a protective gas, 0.52 g (1.2 mmol) of Fe-sarcosine colloid is dissolved in 40 ml of THF in a 250 ml flask, 0.44 g (3.8 mmol) of $AlEt_3$ is added, and 0.08 g (0.4 mmol) of $AuCl_3$ dissolved in 148 ml of THF is added dropwise at 20° C. within 16 h. Any insoluble matter is filtered off through a D4 glass frit, and the solution is freed from any volatile matter in vacuo (0.1 Pa) to obtain 0.45 g of dark red-brown solid Fe/Au colloid (identification No. MK 41). 0.26 g (0.5 mmol of Fe, 0.17 mmol of Au) of this Fe/Au colloid MK 41 is dissolved in 100 ml of THF, and 0.8 g of modifier No. 13 (Table 2) is added to obtain 2.17 g of modified Fe/Au colloid in the form of a black-brown viscous substance. It is soluble in toluene, methanol, ethanol, acetone, THF and ethanol-water mixture (25% by volume of ethanol) (Table 3, No. 28).

EXAMPLE 14

Preparation of Pt Colloid from $PtCl_2$, $AlMe_3$ and Modifier No. 17

The same procedure is used as in Example 2, except that 0.27 g (1 mmol) of $PtCl_2$ in 125 ml of toluene is used, 0.34 g (3 mmol) of $AlMe_3$ as a reductant in 25 ml of toluene is added dropwise at 40° C. within 16 h to obtain 0.42 g of Pt colloid in the form of a black powder (analogous to Table 1, No. 30). 0.3 g (0.7 mmol) of this Pt colloid (analogous to MK 30) is dissolved in 100 ml of toluene, 2.0 g of modifier No. 17 (Table 2) is added at 20° C., and the mixture is stirred for 3 h. There is evolution of 9.1 standard ml of methane (96.1% by volume), and the solution becomes decolorized. The solid is filtered off and dried in vacuo (0.1 Pa) to obtain 2.3 g of a light gray solid powder. A subsequent protolysis with 1 N hydrochloric acid yields 30.7 standard ml of methane (95.7% by volume).

TABLE 1

Starting materials: organometallic-prestabilized nanometal colloids

| | Metal salt | | Reductant | | Solvent | | Conditions | | Product* | | | |
|---|---|---|---|---|---|---|---|---|---|---|---|---|
| No. | Formula | g/mmol | Formula | g/mmol | Formula | ml | T [° C.] | t [h] | m [g] | Metal content, % by weight | Particle size [nm] | Id. # |
| 1 | $Cr(acac)_3$ | 2.5/7.2 | $AlMe_3$ | 3.5/50 | toluene | 100 | 20 | 3 | 2.9 | | | MK 1 |
| 2 | $Fe(acac)_2$ | 2.54/10 | $AlMe_3$ | 2.1/30 | toluene | 100 | 20 | 3 | 2.4 | | | MK 2 |
| 3 | $Co(acac)_2$ | 2.57/10 | $AlMe_3$ | 3.5/50 | toluene | 100 | 60 | 3 | 4.3 | | | MK 3 |
| 4 | $Ni(acac)_2$ | 2.57/10 | $AlMe_3$ | 2.1/30 | toluene | 100 | 20 | 3 | 2.6 | | | MK 4 |

TABLE 1-continued

Starting materials: organometallic-prestabilized nanometal colloids

| | Metal salt | | Reductant | | Solvent | | Conditions | | Product* | | | |
|---|---|---|---|---|---|---|---|---|---|---|---|---|
| No. | Formula | g/mmol | Formula | g/mmol | Formula | ml | T [° C.] | t [h] | m [g] | Metal content, % by weight | Particle size [nm] | Id. # |
| 5 | $Ru(acac)_3$ | 1.99/5 | $AlMe_3$ | 1.05/15 | toluene | 100 | 60 | 24 | 2.0 | Ru: 16.7<br>Al: 11.4 | | MK 5 |
| 6 | $Ru(acac)_3$ | 0.4/1 | $AlEt_3$ | 0.51/4.5 | toluene | 125 | 20 | 16 | 0.8 | Ru: 12.6<br>Al: 15.2 | | MK 6 |
| 7 | $RuCl_3$ | 0.21/1 | $AlEt_3$ | 0.51/4.5 | toluene | 125 | 20 | 16 | 0.6 | Ru: 16.8<br>Al: 20.2 | | MK 7 |
| 8 | $Rh(acac)_3$ | 0.4/1 | $AlMe_3$ | 0.63/9 | toluene | 100 | 60 | 22 | 0.5 | | | MK 8 |
| 9 | $Rh(acac)_3$ | 0.2/0.5 | $AlEt_3$ | 0.26/2.3 | toluene | 65 | 20 | 16 | 0.4 | Rh: 12.9<br>Al: 15.2 | | MK 9 |
| 10 | $RhCl_3$ | 0.11/0.5 | $AlMe_3$ | 0.16/2.3 | toluene | 65 | 40 | 19 | 0.2 | Rh: 25<br>Al: 30.4 | | MK 10 |
| 11 | $RhCl_3$ | 0.21/1 | $AlEt_3$ | 0.51/4.5 | toluene | 125 | 20 | 16 | 0.62 | Rh: 16.6<br>Al: 19.6 | | MK 11 |
| 12 | $RhCl_3$ | 0.77/3.1 | $AlOct_3$ | 4.1/11.1 | THF | 150 | 40 | 18 | 4.5 | Rh: 8.5<br>Al: 6.7 | 2–3 | MK 12 |
| 13 | $Pd(acac)_2$ | 0.3/1 | $AlMe_3$ | 0.14/2 | THF | 300 | 20 | 5 | 0.39 | Pd: 27<br>Al: 14 | | MK 13 |
| 14 | $Pd(acac)_2$ | 0.29/0.94 | $AlEt_3$ | 0.21/1.9 | toluene | 250 | 20 | 18 | 0.4 | Pd: 22<br>Al: 13 | | MK 14 |
| 15 | $PdCl_2$ | 0.18/1 | $AlEt_3$ | 0.26/2.25 | toluene | 250 | 20 | 4 | 0.42 | Pd: 23.2<br>Al: 21.3 | | MK 15 |
| 16 | Ag<br>neodecanoate | 9.3/21.5 | $AlOct_3$ | 8.0/21.8 | toluene | 1000 | 20 | 36 | 17.1 | Ag: 11.8<br>Al: 2.7 | 8–12 | MK 16 |
| 17 | $ReCl_5$ | 0.36/1 | LiBut | 0.32/5 | THF | 100 | 60 | 36 | 0.5 | | | MK 17 |
| 18 | $ReCl_5$ | 0.364/1 | $NaAlEt_4$ | 0.83/5 | toluene | 150 | 60 | 90 | 0.6 | | | MK 18 |
| 19 | $Ir(acac)_3$ | 0.25/0.5 | $AlMe_3$ | 0.16/2.25 | toluene | 65 | 60 | 16 | 0.35 | Ir: 27.5<br>Al: 17.4 | | MK 19 |
| 20 | $Ir(acac)_3$ | 0.49/1 | $AlEt_3$ | 0.51/4.5 | toluene | 125 | 80 | 16 | 0.9 | Ir: 21.4<br>Al: 13.5 | | MK 20 |
| 21 | $IrCl_3$ | 0.3/1 | $AlEt_3$ | 0.51/4.5 | toluene | 125 | 80 | 16 | 0.7 | Ir: 27.5<br>Al: 17.4 | | MK 21 |
| 22 | $Pt(acac)_2$ | 7.88/20 | $AlMe_3$ | 4.32/60 | toluene | 200 | 40 | 24 | 8.3 | Pt: 42.3<br>Al: 17.5 | | MK 22 |
| 23 | $Pt(acac)_2$ | 3.9/10 | $AlEt_3$ | 3.4/30 | toluene | 1000 | 20 | 16 | 6.4 | Pt: 32.7<br>Al: 10.6 | 1.0 | MK 23 |
| 24 | $Pt(acac)_2$ | 0.39/1 | $AlBut_3$ | 0.59/3 | toluene | 125 | 20 | 16 | 0.86 | Pt: 24.5<br>Al: 12.9 | | MK 24 |
| 25 | $Pt(acac)_2$ | 0.38/1 | $HAlEt_2$ | 0.26/3 | toluene | 100 | 20 | 23 | 0.3 | | | MK 25 |
| 26 | $Pt(acac)_2$ | 0.38/1 | $NaAlEt_4$ | 0.50/3 | toluene | 100 | 60 | 12 | 0.8 | | | MK 26 |
| 27 | $Pt(acac)_2$ | 0.38/1 | $MgEt_2$ | 1.2/14.6 | toluene | 100 | 20 | 21 | 1.2 | Pt: 14.9<br>Mg: 20.8 | | MK 27 |
| 28 | $Pt(acac)_2$ | 0.38/1 | $ZnEt_2$ | 0.37/3 | toluene | 100 | 20 | 27 | 0.5 | | | MK 28 |
| 29 | $PtCl_2$ | 0.27/1 | $AlMe_3$ | 0.21/3 | toluene | 100 | 20 | 22 | 0.4 | | | MK 29 |
| 30 | $PtCl_2$ | 0.27/1 | $AlMe_3$ | 0.34/3 | toluene | 125 | 40 | 16 | 0.47 | Pt: 41.1<br>Al: 15.2 | 2.0 | MK 30 |
| 31 | $PtCl_2$ | 0.27/1 | $AlEt_3$ | 0.34/3 | toluene | 125 | 20 | 16 | 0.52 | Pt: 43<br>Al: 13.6 | 2.0 | MK 31 |
| 32 | $PtCl_2$ | 0.27/1 | $AlBut_3$ | 0.59/3 | toluene | 125 | 20 | 16 | 0.74 | Pt: 26.4<br>Al: 10.9 | | MK 32 |
| 33 | $PtCl_2$ | 1.0/3.75 | $AlOct_3$ | 2.7/7.5 | THF | 300 | 20 | 16 | 3.5 | Pt: 20.9<br>Al: 5.8 | | MK 33 |
| 34 | $Fe(acac)_2$<br>$Co(acac)_2$ | 2.54/10<br>1.29/5 | $AlMe_3$ | 5.4/75 | toluene | 200 | 20 | 3 | 4.9 | | | MK 34 |
| 35 | $Pd(acac)_2$<br>$Pt(acac)_2$ | 0.54/1.8<br>0.09/0.24 | $AlEt_3$ | 0.46/4 | toluene | 500 | 20 | 2 | 0.85 | Pd: 22<br>Pt: 5.5<br>Al: 12.7 | 3.2 | MK 35 |
| 36 | $Pt(acac)_2$<br>$Ru(acac)_3$ | 7.86/20<br>7.96/20 | $AlMe_3$ | 8.64/120 | toluene | 400 | 60 | 21 | 17.1 | Pt: 20.6<br>Ru: 10.5<br>Al: 19.6 | | MK 36 |
| 37 | $Pt(acac)_2$<br>$Ru(acac)_3$ | 1.92/5<br>1.99/5 | $AlMe_3$ | 3.5/50 | toluene | 100 | 60 | 25 | 5.1 | | 1.3 | MK 37 |
| 38 | $PtCl_2$<br>$RuCl_3$ | 0.27/1<br>0.21/1 | $AlMe_3$ | 0.43/6 | toluene | 100 | 60 | 22 | 0.5 | | 1.3 | MK 38 |
| 39 | $Pt(acac)_2$<br>$SnCl_2$ | 1.15/2.9<br>0.19/1 | $AlMe_3$ | 0.86/12 | toluene | 100 | 60 | 2 | 1.1 | Pt: 27.1<br>Sn: 5.2<br>Al: 14.4 | | MK 39 |
| 40 | $Pt(acac)_2$ | 3.83/10 | $AlMe_3$ | 2.2/30 | toluene | 100 | 40 | 3 | 6.1 | Pt: 30.9<br>Al: 13.4 | | protolysis |

*may contain residual solvent

TABLE 2

| Modifiers | | | |
|---|---|---|---|
| No. | Substance class | Name | Trade name |
| 1 | alcohol | 1-decanol | |
| 2 | carboxylic acid | 2-hydroxypropionic acid | DL-lactic acid |
| 3 | carboxylic acid | cis-9-octadecenoic acid | oleic acid |
| 4 | silanol | triphenylsilanol | |
| 5 | sugar | D-(+)-glucose | grape sugar |
| 6 | polyalcohol | polyethylene glycol 200 | PEG 200 |
| 7 | vinyl pyrrolidone polymerizate | polyvinyl pyrrolidone K30 | PVP, Polyvidon, Povidon |
| 8 | surfactant, cationic | di(hydrotallow)dimethylammonium chloride | Arquad 2HT-75 |
| 9 | surfactant, cationic | 3-chloro-2-hydroxypropyldimethyl-dodecylammonium chloride | Quab 342 |
| 10 | surfactant, amphiphilic betaine | lauryldimethylcarboxymethylammonium betaine | Rewoteric AM DML |
| 11 | surfactant, anionic | Na cocoamidoethyl-N-hydroxyethylglucinate | Dehyton G |
| 12 | surfactant, non-ionic | decaethylene glycol hexadecyl ether | Brij 56 |
| 13 | surfactant, non-ionic | polyethylene glycol dodecyl ether | Brij 35 |
| 14 | surfactant, non-ionic | polyoxyethylene sorbitane monolaurate | Tween 20 |
| 15 | surfactant, non-ionic | polyoxyethylene sorbitane monopalmitate | Tween 40 |
| 16 | active charcoal | | |
| 17 | silica | | silica gel 60 |
| 18 | alumina | | |

TABLE 3

Modification of organometallic-prestabilized metal colloids

| | Metal colloid | | | | Solvent | | Modifier Table 2, | | Temp. | Time | Product* | Metal content | Dispersing properties | | | | | | |
|---|---|---|---|---|---|---|---|---|---|---|---|---|---|---|---|---|---|---|---|
| No. | Metal | Id. # | mmol | m [g] | Name | ml | No. | m [g] | T [° C.] | t [h] | m [g] | % | A | B | C | D | E | F | G |
| 1 | Cr | MK 1 | 1 | 0.52 | THF | 200 | 13 | 2.0 | 60 | 16 | 3.2 | | − | + | + | + | − | − | − |
| 2 | Fe | MK 2 | 0.5 | 0.12 | THF | 100 | 1 | 2.0 | 60 | 16 | 2.0 | | + | + | + | + | − | + | − |
| 3 | Co | MK 3 | 1 | 0.43 | THF | 100 | 13 | 2.0 | 60 | 16 | 2.1 | | − | + | + | + | − | − | − |
| 4 | Ni | MK 4 | 1 | 0.39 | THF | 100 | 13 | 2.0 | 60 | 16 | 1.1 | | − | + | + | + | + | − | − |
| 5 | Rh | MK 8 | 0.5 | 0.25 | THF | 100 | 13 | 1.0 | 20 | 16 | 1.3 | | − | − | + | + | + | − | |
| 6 | Pd | MK 13 | 1 | 0.39 | THF | 300 | 13 | 1.0 | 20 | 16 | 1.4 | | − | + | + | − | + | − | − |
| 7 | Pt | MK 22 | 0.25 | 0.1 | THF | 25 | 1 | 2.5 | 60 | 16 | 2.6 | | + | + | + | − | − | + | − |
| 8 | Pt | MK 22 | 0.5 | 0.21 | THF | 100 | 2 | 1.5 | 60 | 16 | 1.2 | | − | − | − | + | − | − | − |
| 9 | Pt | MK 22 | 0.5 | 0.21 | THF | 100 | 3 | 1.5 | 60 | 16 | 1.4 | | + | + | + | − | − | + | − |
| 10 | Pt | MK 22 | 0.5 | 0.21 | THF | 100 | 5 | 1.5 | 60 | 16 | 1.0 | | − | − | − | − | − | − | + |
| 11 | Pt | MK 22 | 0.5 | 0.21 | THF | 100 | 6 | 0.8 | 60 | 16 | 0.9 | | − | − | − | − | − | − | + |
| 12 | Pt | MK 22 | 0.5 | 0.21 | THF | 100 | 7 | 1.5 | 60 | 16 | 1.2 | | − | − | − | − | − | − | + |
| 13 | Pt | MK 22 | 0.2 | 0.08 | THF | 25 | 8 | 2.0 | 60 | 16 | 2.0 | | − | − | + | + | − | − | − |
| 14 | Pt | MK 22 | 0.5 | 0.21 | THF | 100 | 9 | 1.5 | 60 | 16 | 1.2 | | − | + | + | + | − | − | + |
| 15 | Pt | MK 22 | 0.2 | 0.08 | THF | 25 | 10 | 2.0 | 60 | 16 | 2.1 | | − | − | + | + | − | − | + |
| 16 | Pt | MK 22 | 0.2 | 0.08 | THF | 25 | 11 | 2.0 | 60 | 16 | 2.05 | | − | − | − | − | − | − | + |
| 17 | Pt | MK 22 | 0.25 | 0.105 | THF | 25 | 12 | 2.5 | 60 | 16 | 2.8 | | − | + | − | + | + | − | − |
| 18 | Pt | MK 22 | 0.5 | 0.21 | THF | 100 | 13 | 0.4 | 20 | 16 | 0.5 | Pt: 9.3<br>Al: 5.6 | − | − | + | + | − | − | + |
| 19 | Pt | MK 22 | 0.5 | 0.21 | THF | 100 | 14 | 0.8 | 60 | 16 | 0.81 | Pt: 8.5<br>Al: 2.4 | − | − | + | − | − | − | + |
| 20 | Pt | MK 22 | 0.2 | 0.08 | THF | 25 | 15 | 2.0 | 60 | 16 | 2.03 | | − | + | + | + | + | − | + |
| 21 | Pt | MK 23 | 0.33 | 0.2 | THF | 100 | 13 | 0.53 | 60 | 16 | 0.51 | | − | + | + | + | − | − | + |
| 22 | Pt | MK 25 | 0.33 | 0.1 | THF | 100 | 13 | 1.0 | 20 | 16 | 1.7 | | − | + | + | + | + | − | + |
| 23 | Pt | MK 26 | 0.5 | 0.35 | THF | 100 | 13 | 2.0 | 60 | 16 | 1.0 | | − | + | + | + | + | − | + |
| 24 | Pt | MK 27 | 0.5 | 0.56 | THF | 100 | 13 | 2.0 | 60 | 16 | 2.6 | Pt: 4.6<br>Mg: 5.6 | − | + | + | + | + | − | + |
| 25 | Pt | MK 29 | 0.9 | 0.15 | THF | 200 | 1 | 1.2 | 60 | 16 | 1.5 | | + | + | + | − | − | + | − |
| 26 | Pt | MK 30 | 1.0 | 0.47 | toluene | 100 | 4 | 1.0 | 60 | 3 | 1.3 | Pt: 11.0<br>Al: 3.9 | − | + | + | − | + | − | − |
| 27 | $Fe_2Co$ | MK 34 | 0.5 | 0.136 | THF | 100 | 1 | 1.5 | 60 | 16 | 1.6 | | + | + | + | − | − | + | − |
| 28 | FeAu | MK 41 | 0.5/0.17 | 0.26 | THF | 100 | 13 | 0.8 | 60 | 16 | 2.17 | | − | + | + | + | + | − | +** |
| 29 | PtRu | MK 36 | 1.0/1.0 | 0.94 | THF | 100 | 13 | 2.0 | 60 | 16 | 3.2 | Pt: 6.3<br>Ru: 3.0<br>Al: 5.1 | − | + | + | + | + | − | + |
| 30 | $Pt_3Sn$ | MK 39 | 0.5/0.17 | 0.36 | THF | 200 | 13 | 1.0 | 60 | 16 | 1.4 | Pt: 6.8<br>Sn: 1.2<br>Al: 3.2 | − | + | + | + | + | − | + |

*may contain residual solvent; **ethanol-water mixture (25% by volume of ethanol)

A = hydrocarbons, B = aromatics, C = ethers, D = alcohols, E = ketones, F = pump oils (Shell Vitrea Oil 100, Shell), G = water and aqueous solutions, + = solubility >100 mmol/l, − = insoluble

What is claimed is:

1. A process for preparing modified nanoscale transition metal or alloy colloids which are dispersible in hydrophobic and/or hydrophilic organic solvents and/or water, said process comprising:

a) providing starting materials which have been prepared either by:

i) reacting compounds of Periodic Table groups 6 to 11 transition metals with organoelement compounds of metals of Periodic Table groups 1, 2, 12 and 13; or ii) treating presynthesized nanoscale transition metal or alloy colloids with organoelement compounds of metals of Periodic Table groups 1, 2, 12 and 13;

to form an organometallic protective shell containing said metal of Periodic Table groups 1, 2, 12 and 13; and b) reacting said starting materials, in situ or after isolation, with an organic or inorganic modifier which reacts with said protective shell protolytically or with the insertion of C/C, C/N or C/O multiple bonds or through Lewis, acid-base interactions, without degradation of the colloids.

2. The process according to claim 1, wherein the dispersibility of said colloids in said solvent is >20 mmol/l.

3. The process according to claim 2, wherein the dispersibility of said colloids in said solvent is >100 mmol/l.

4. The process according to claim 1, wherein said Periodic Table group 6 to 11 transition metal compounds are one or more compounds selected from the group consisting of metal salts, halides, pseudohalides, alcoholates, carboxylates and acetylacetonates.

5. The process according to claim 1, wherein said presynthesized colloids are transition metal or alloy colloids of transition metals of Periodic Table groups 6 to 11 or precious-metal anticorrosion-protected colloids of Fe, Co or Ni or their alloys.

6. The process according to claim 1, wherein said modifier is selected from the group consisting of alcohols, carboxylic acids, polymers, polyethers, polyalcohols, polysaccharides, sugars, surfactants, silanols, active charcoals, inorganic oxides and hydroxides.

7. Nanoscale transition metal or alloy colloids obtained by the process according to claim 1.

8. The nanoscale transition metal or alloy colloids according to claim 7, which are of a transition metal selected from the group consisting of Cr, Fe, Co, Ni, Rh, Pd and Pt of of an alloy selected from the group consisting of Fe/Co, Fe/Au, Pt/Ru and Pt/Sn.

9. The nanoscale transition metal or alloy colloids according to claim 7, which have an average particle diameter of <2 nm.

10. The nanoscale transition metal or alloy colloids according to claim 7, which are dispersible in hydrocarbons, aromatics, ethers, alcohols, ketones, pump oils, water and/or aqueous solutions.

11. A method of coating a surface comprising coating said surface with nanoscale transition metal or alloy colloids according to claim 7.

12. A method of conducting a sol-gel process comprising conducting said sol-gel process in the presence of nanoscale transition metal or alloy colloids according to claim 7.

13. A method of conducting a hydrogenation reaction comprising conducting said hydrogenation reaction in the presence of a hydrogenation catalyst comprising nanoscale transition metal or alloy colloids according to claim 7.

14. A method of conducting an oxygen transfer reaction comprising conducting said oxygen transfer reaction in the presence of a catalyst comprising optionally supported nanoscale transition metal or alloy colloids according to claim 7.

15. A method of conducting a fuel cell reaction comprising conducting said fuel cell reaction in the presence of an electrocatalyst comprising optionally supported nanoscale transition metal or alloy colloids according to claim 7.

16. The method according to claim 15, wherein the colloids are Pt/Ru colloids.

17. The method according to claim 15, wherein the colloids are Pt/Sn colloids.

18. A method of storing information on a magneto-optical storage medium comprising storing said information on a magneto-optical storage medium comprising nanoscale transition metal or alloy colloids according to claim 7, said colloids being Fe, Co or Ni colloids or their alloy colloids.

19. A method of forming a magnetic fluid seal comprising forming a magnetic fluid seal with a magnetic fluid comprising nanoscale transition metal or alloy colloids according to claim 7, said colloids being Fe, Co or Ni colloids or their alloy colloids.

20. A method of separating cells magnetically comprising separating cells magnetically marked with a magnetic marker comprising nanoscale transition metal or alloy colloids according to claim 7, said colloids being Fe colloids or Fe alloy colloids.

21. A method of conducting a magnetic fluid hyperthermia process comprising conducting said magnetic fluid hyperthermia process with a magnetic fluid comprising nanoscale transition metal or alloy colloids according to claim 7, optionally after treatment with oxygen, said colloids being Fe colloids or Fe alloy colloids.

22. A method of ink-jet printing comprising ink-jet printing with a metallic ink comprising nanoscale transition metal or alloy colloids according to claim 7.

23. The method according to claim 22, wherein the colloids are Pt colloids or Pt alloy colloids.

24. A method of laser sintering comprising laser sintering a substance comprising nanoscale transition metal or alloy colloids according to claim 7.

25. The method according to claim 24, wherein the colloids are Pt colloids or Pt alloy colloids.

* * * * *